US00PP33619P2

(12) United States Plant Patent
Holtmaat

(10) Patent No.: US PP33,619 P2
(45) Date of Patent: Nov. 2, 2021

(54) ***ECHINACEA* PLANT NAMED 'BLU481'**

(50) Latin Name: ***Echinacea* hybrid**
Varietal Denomination: BLU481

(71) Applicant: Henricus Maria Joseph Holtmaat, Zuidwolde (NL)

(72) Inventor: Henricus Maria Joseph Holtmaat, Zuidwolde (NL)

(73) Assignee: AB-KWEKERSRECHTEN BV, Zuidwolde (NL)

( * ) Notice: Subject to any disclaimer, the term of this patent is extended or adjusted under 35 U.S.C. 154(b) by 0 days.

(21) Appl. No.: 17/185,902

(22) Filed: Feb. 25, 2021

(30) Foreign Application Priority Data

Oct. 7, 2020 (QZ) ..... PBR 2020/2457

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 6/1448; A01H 5/02
See application file for complete search history.

*Primary Examiner* — Keith O. Robinson
(74) *Attorney, Agent, or Firm* — Penny J. Aguirre

(57) ABSTRACT

A new cultivar of *Echinacea* plant named 'BLU481' that is characterized by its inflorescences with ray florets that are deep red-purple in color and its 'BLU481' exhibits conspicuous inflorescences with disc florets that are deep red-purple in color and changing to a slightly lighter color at the tip.

2 Drawing Sheets

Botanical classification: *Echinacea* hybrid.
Variety denomination: 'BLU481'.

CROSS-REFERENCE TO A RELATED APPLICATION

This application claims priority to European Community Plant Variety Office (CPVO) Plant Breeder's Rights Application No. 2020/2457 filed on Oct. 7, 2020, under 35 U.S.C. 119(f), the entire contents of which is incorporated by reference herein.

BACKGROUND OF THE INVENTION

The present invention relates to a new and distinct cultivar of *Echinacea* of hybrid origin and will be referred to hereafter by its cultivar name, 'BLU481'. 'BLU481' represents a new cultivar of coneflower, an herbaceous perennial grown for landscape use.

The new cultivar arose from an ongoing breeding program by the Inventor in Zuidwolde, The Netherlands with the objective of selecting new cultivars of *Echinacea* with strong plant habits, unique inflorescence colors and enlarged disc florets. The new cultivar was selected as a unique seedling in a trial field by the Inventor in July of 2018. The trial field had been planted with seed collected from numerous cultivars and proprietary *Echinacea* seedlings from the Inventor's breeding program. The parentage of 'BLU481' is therefore unknown.

Asexual propagation of the new cultivar was first accomplished by tissue culture using meristematic tissue in Heerhugowaard, The Netherlands in March of 2019 under the direction of the Inventor. Asexual propagation by tissue culture has determined that the characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'BLU481' as a unique cultivar of *Echinacea*.

1. 'BLU481' exhibits inflorescences with ray florets that are deep red-purple in color.
2. 'BLU481' exhibits conspicuous inflorescences with disc florets that are deep red-purple in color and changing to a slightly lighter color towards the tip.

The new cultivar can be most closely compared to the cultivars 'Drop352' (U.S. Plant Pat. No. 30,378) and 'Pink Double Delight' (U.S. Plant Pat. No. 18,803). 'Drop352' and 'Pink Double Delight' are both similar to 'BLU481' in inflorescence shape. 'Drop352' differs from 'BLU481' in having ray florets that are yellow-green in color, disc florets that are yellow-orange and fading to yellow-green in color, and inflorescences that are larger in size. 'Pink Double Delight' differs from 'BLU481' in having ray florets that are red-purple to grey-purple in color, and disc florets that red-purple in color the entire floret (not changing color towards the tip) and in producing more inflorescences per plant.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102(b)(1). Disclosures include but may not be limited to website listing by AB cultivars.

BRIEF DESCRIPTION OF THE DRAWINGS

The plants in the accompanying photographs depict the characteristics of a one-year-old plant of 'BLU481' as grown in a 19-cm container in Zuidwolde, The Netherlands.

The photograph in FIG. 1 provides a side view of 'BLU481' in bloom.

Figure 1:
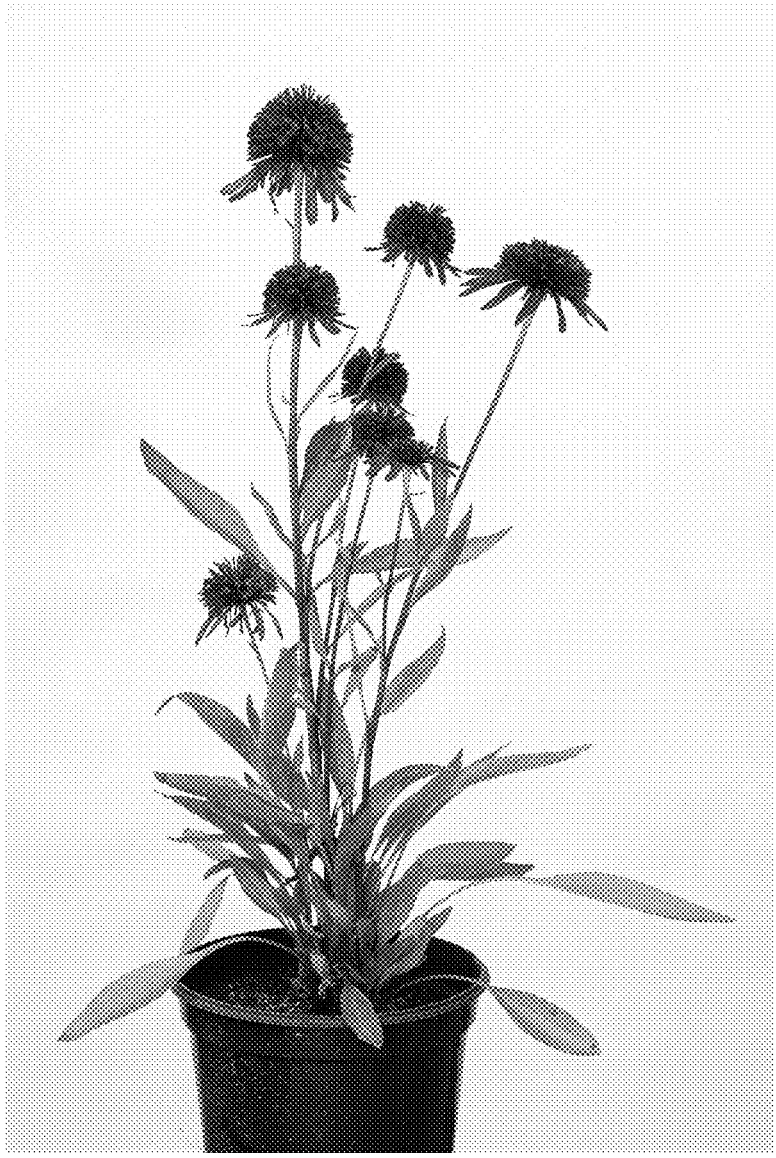
Figure 2:
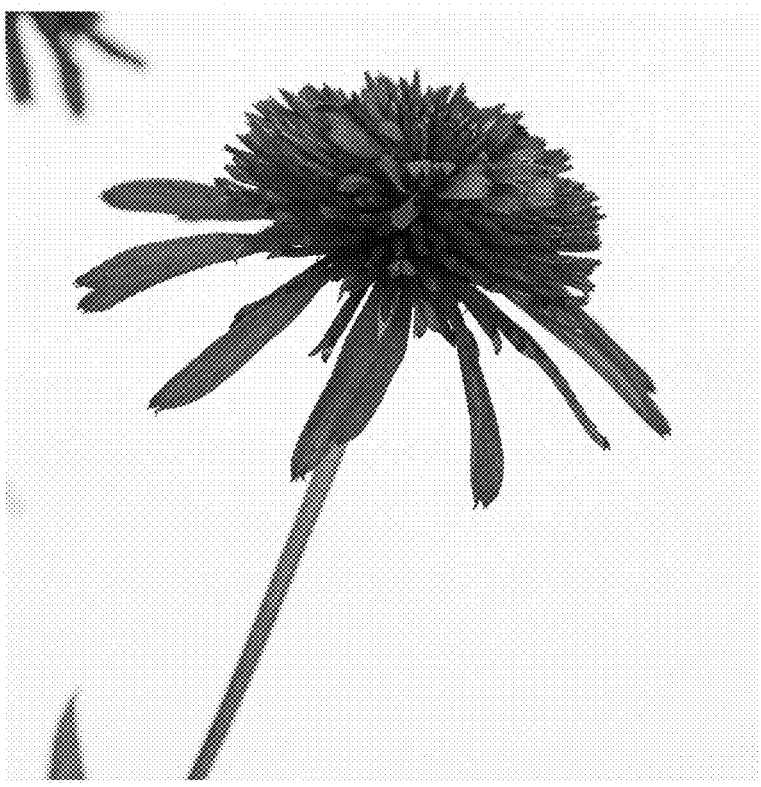

The photograph in FIG. 2 provides a close-up view of an inflorescence of 'BLU481'.

Figure 3:
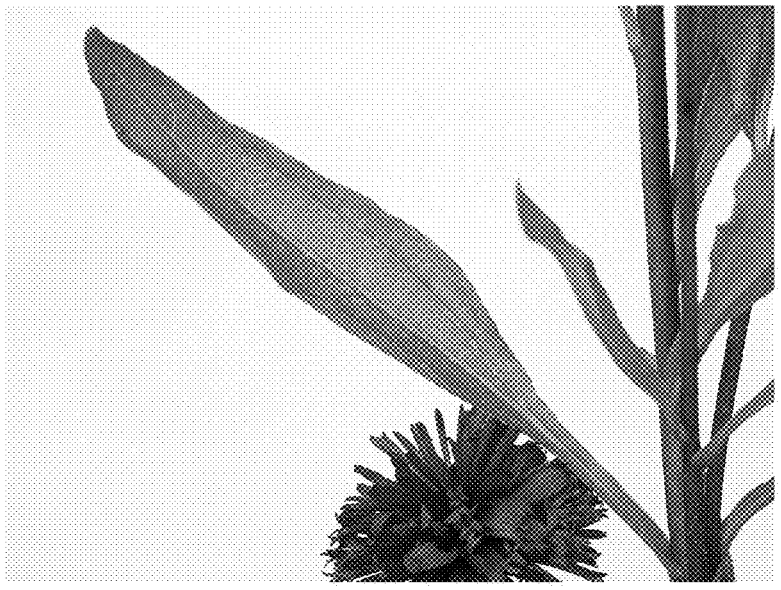

The photograph in FIG. 3 provides a close-up view of a leaf of 'BLU481'.

The colors in the photograph may differ slightly from the color values cited in the detailed botanical description, which accurately describe the colors of the new *Echinacea*.

BOTANICAL DESCRIPTION OF THE PLANT

The plants in the accompanying photographs depict the characteristics of one-year-old plants of 'BLU481' as grown in a 19-cm containers in Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Approximately 10 weeks from summer and late summer (July until late September) in The Netherlands.

*Plant type*.—Herbaceous perennial.

*Plant shape*.—Narrow oblong to narrow ovate.

*Plant habit*.—Clump forming with strong stems held upright.

*Height and spread*.—Average of 61.2 cm in height, 38.5 cm in width, reaches an average of 70 cm in height and 45 cm in width as a mature plant in the landscape.

*Hardiness*.—U.S.D.A. Zones 4 to 9.

*Diseases and pests*.—No resistance or susceptibility to pests or diseases has been observed.

*Root description*.—Fibrous.

*Propagation*.—Tissue culture.

*Root development*.—An average of 10 weeks for rooting with a finished plant produced in about 3 months.

*Growth rate*.—Moderately vigorous.

Stem description:

*Shape*.—Rounded.

*Stem color*.—Ranging between 183A and 187A, shaded sides strongly tinged 152C.

*Stem size*.—Average of 4 mm in diameter and an average of 10.3 cm in length.

*Stem surface*.—Rough to the touch, moderately covered with short strigose hairs; 0.4 mm in length, 156D in color.

*Stem strength*.—Strong.

*Stem aspect*.—Stems grow in an average angle of 10° from the base (0°=vertical).

*Branching*.—Main flowering stems grow from the base with a few lateral branches present, average of 2 primary branches, 3 lateral branches per primary stem.

Foliage description:

*Leaf shape*.—Narrow ovate to narrow elliptic.

*Leaf division*.—Simple.

*Leaf base*.—Attenuate.

*Leaf apex*.—Narrowly acute.

*Leaf venation*.—Pinnate, upper surface; 152D, lower surface; 146C to 146D.

*Leaf margins*.—Entire, very slightly and coarsely undulate.

*Leaf attachment*.—Petiolate.

*Leaf arrangement*.—Alternate.

*Internode length*.—An average of 3.5 cm.

*Leaf size*.—Basal leaves; 12.3 cm in length, 3.7 cm in width, cauline leaves; 10.5 cm in length, 2.6 cm in width.

*Leaf color*.—Young upper surface; between 137B and 143A, young lower surface; 146B, mature upper surface; 137B, tinged with 146B, mature lower surface; 146A to 146B.

*Leaf surface*.—Both surfaces are slightly glossy, non-rugose, rough to the touch and moderately covered with very short strigose hairs; average length of 0.3 mm and 156D in color.

*Petioles*.—On basal leaves an average of 17 cm in length and 2.5 mm in diameter, on cauline stem leaves V-shaped an average of 2.3 cm in length and 4 mm in diameter, surface is smooth and moderately covered with very short strigose hairs 0.3 mm in length and too small to measure color, color; upper surface 178B, changing to 152B at the distal end, base 183A, lower part of the base 187C, lower surface 182B, changing to 150C at the distal end, 187C at the base.

Inflorescence description:

*Type*.—Terminal capitulum, heterogamous with ray florets around the head margin and anemone-type disc florets in the center.

*Capitulum number*.—One terminal capitulum per lateral branch.

*Lastingness of inflorescence*.—About four weeks.

*Capitulum size*.—Matures to about 4.5 cm in height and 10.2 cm in diameter, disk is an average of 6.2 cm in diameter.

*Fragrance*.—None.

*Involucral bracts or phyllary*.—Average of 32 arranged in 2 rows, up to 8 mm in length and 2 mm in width, cuneate base, acute apex, ovate in shape, entire margins moderately, held in an average angle of −90° to horizontal, color; upper surface 138A, margins 137A, lower surface 137D, upper surface smooth, glabrous, matte, lower surface smooth, matte, sparsely covered with very short hairs, margins moderately covered with very short hairs, average length of hairs 0.3 mm, too small to measure color.

*Buds*.—Flattened globular in shape, up to 2.4 cm in diameter and 2.1 cm in length, color; 187A, immature ray florets 186A.

*Peduncle*.—Strong, straight on top of main (flowering) stem, average of 15.5 cm in length, 3 mm in diameter, color; 183A, shaded side tinged 177A, distal end 144A, surface is moderately covered with very short hairs an average length of 0.3 mm in length, N155A in color.

*Ray florets*.—Rotate, average of 16, whorled, oblanceolate in shape, average of 4.6 cm in length and 9 mm in width, praemorse apex, cuneate base, entire margin, moderately drooping in an average angle of −20°, upper surface matte, velvety and glabrous, lower surface very slightly glossy, sparsely pubescent, color; upper surface when opening 61A, lower surface when opening between 59A and 59B, upper surface when fully open 71A, lower surface when fully open 59A to 59B, tinged 200D at the top, upper surface fading to 184B, lower surface fading to 184B, veins 184A.

*Disc florets*.—Numerous, average of 240, disc florets on lower ⅔rd of disc are tubular in shape, lower 85% fused, disc florets on upper ⅓rd of disc are broadly oblong to obovate in shape, base fused, fused into tube, arranged spirally on disc, average of 2 cm in length and 4.5 mm in width, entire margin, both surfaces smooth and matte, color; upper surface when opening and fully open; disc florets on lower ⅔rd of disc 60B, disc florets on upper ⅓rd of disc in between 60B and 61B, lower surface when opening; disc florets on lower ⅔rd of disc 59B, disc florets on upper ⅓rd of disc 59B, tube 182C, lower surface when fully open; disc florets on lower ⅔rd of disc 59A, tube 182A, disc florets on upper ⅓rd of disc 59B, base 185C.

*Receptacle*.—Narrow deltoid in shape, average of 1.4 cm in height and 9 mm in diameter, 187A to 187B in color.

*Receptacle spines*.—An average of 240 per disc floret, acicular in shape, acute apex, attenuate base, 1.2 cm in length, 2 mm in diameter, smooth and glossy surface, color: apex; N34A changing to 13A at the mid-section of apex, mid-section; 146D, base; 157B.

Reproductive organs (present on disc florets only):

*Gynoecium*.—Pistil; 1, 8 mm in length, stigma; unequal, decurrent, 1 mm in length, 2 mm in diameter, 180A, style; 6.5 mm in length and 183D in color, ovary; 157A in color.

*Androecium*.—Stamens; 5, filaments; 1 mm in length, 182A in color, anther; linear in shape, 2 mm in length and 174D in color, pollen; none.

*Fruit/seed*.—No fruit or seed detected to date.

It is claimed:

1. A new and distinct cultivar of *Echinacea* plant named 'BLU481' substantially as herein illustrated and described.

* * * * *